(12) United States Patent
Heege et al.

(10) Patent No.: US 10,603,231 B2
(45) Date of Patent: Mar. 31, 2020

(54) METHOD AND APPARATUS FOR MANUFACTURING A TAMPON PACKAGING

(71) Applicant: ONTEX BVBA, Buggenhout (BE)

(72) Inventors: Rudolf Heege, Kaisersesch (DE); Thomas Heege, Mayen (DE)

(73) Assignee: Ontex BVBA, Buggenhout (BE)

( * ) Notice: Subject to any disclaimer, the term of this patent is extended or adjusted under 35 U.S.C. 154(b) by 136 days.

(21) Appl. No.: 15/774,378

(22) PCT Filed: Nov. 9, 2016

(86) PCT No.: PCT/EP2016/077138
§ 371 (c)(1),
(2) Date: May 8, 2018

(87) PCT Pub. No.: WO2017/081077
PCT Pub. Date: May 18, 2017

(65) Prior Publication Data
US 2019/0337648 A1    Nov. 7, 2019

(30) Foreign Application Priority Data

Nov. 9, 2015 (EP) .................................. 15193734

(51) Int. Cl.
| | | |
|---|---|---|
| B65B 5/02 | (2006.01) | |
| A61F 13/551 | (2006.01) | |
| B29C 65/18 | (2006.01) | |
| B29C 65/78 | (2006.01) | |
| B29C 65/00 | (2006.01) | |
| B65B 5/04 | (2006.01) | |

(Continued)

(52) U.S. Cl.
CPC ........ *A61F 13/55175* (2013.01); *B29C 65/18* (2013.01); *B29C 65/7885* (2013.01);
(Continued)

(58) Field of Classification Search
CPC .......... B65B 5/024; B65B 5/04; B65B 19/34; B65B 51/26; A61F 13/55175; B31B 50/32; B31B 50/322; B31B 50/324; B31B 70/30
(Continued)

(56) References Cited

U.S. PATENT DOCUMENTS 2,580,456 A * 1/1952 Noe .................. B65B 19/34
53/545
2,697,385 A * 12/1954 O'Neil .................. B31B 50/00
493/269
(Continued)

FOREIGN PATENT DOCUMENTS

DE     1136565 B  *  9/1962  ............. B65H 19/28
DE     1204062 B  * 10/1965  ............. B31B 50/00
(Continued)

OTHER PUBLICATIONS

Extended European Search Report in European App. No. 15193734. 9, dated Feb. 10, 2016.
(Continued)

*Primary Examiner* — Stephen F. Gerrity
(74) *Attorney, Agent, or Firm* — Vivicar Law, PLLC

(57) ABSTRACT

A method and apparatus for manufacturing a tampon packaging where the packaging is manufactured separately from the tampon. A first transversal end is overlapped with a second transversal end of a strip of heat-sealable film. The first transversal end is heat sealed to the second transversal end of the heat-sealable film, thereby forming a tube of film.

19 Claims, 7 Drawing Sheets

(51) Int. Cl.
  *B65B 19/34* (2006.01)
  *B65B 51/26* (2006.01)
  *B29L 31/48* (2006.01)
  *B29L 31/00* (2006.01)

(52) U.S. Cl.
  CPC ...... *B29C 66/1122* (2013.01); *B29C 66/4322* (2013.01); *B29C 66/43121* (2013.01); *B29C 66/49* (2013.01); *B29C 66/73921* (2013.01); *B29C 66/81419* (2013.01); *B29C 66/849* (2013.01); *B29C 66/851* (2013.01); *B65B 5/024* (2013.01); *B65B 5/04* (2013.01); *B65B 19/34* (2013.01); *B65B 51/26* (2013.01); *B29L 2031/4878* (2013.01); *B29L 2031/712* (2013.01)

(58) Field of Classification Search
  USPC ........... 53/563; 493/205, 303, 305, 306, 308
  See application file for complete search history.

(56) References Cited

U.S. PATENT DOCUMENTS

| | | | |
|---|---|---|---|
| 3,057,126 A * | 10/1962 | Chalmers et al. | B65B 19/02 53/563 |
| 3,777,632 A | 12/1973 | Pepmeier | |
| 4,583,964 A | 4/1986 | Warncke | |
| 4,617,781 A * | 10/1986 | Ingersoll | B29C 65/18 156/219 |
| 4,655,738 A * | 4/1987 | Jansson | B31B 50/00 53/563 |
| 5,371,999 A | 12/1994 | Hansen et al. | |
| 5,442,897 A * | 8/1995 | Hinzmann et al. | B65B 5/02 53/563 |
| 5,533,323 A | 7/1996 | Osti et al. | |
| 7,322,919 B2 * | 1/2008 | Malini | B29C 53/44 53/563 |
| 2003/0233813 A1 * | 12/2003 | Leslie et al. | A61F 13/55175 53/452 |
| 2010/0130954 A1 | 5/2010 | Handel et al. | |

FOREIGN PATENT DOCUMENTS

| | | | |
|---|---|---|---|
| DE | 1288416 B * | 1/1969 | .............. B31B 50/00 |
| DE | 3218331 A1 | 11/1983 | |
| EP | 0970888 A1 | 1/2000 | |
| EP | 1477406 A1 | 11/2004 | |

OTHER PUBLICATIONS

PCT Search Report and Written Opinion for PCT/EP2016/077138, dated Dec. 12, 2016.

* cited by examiner

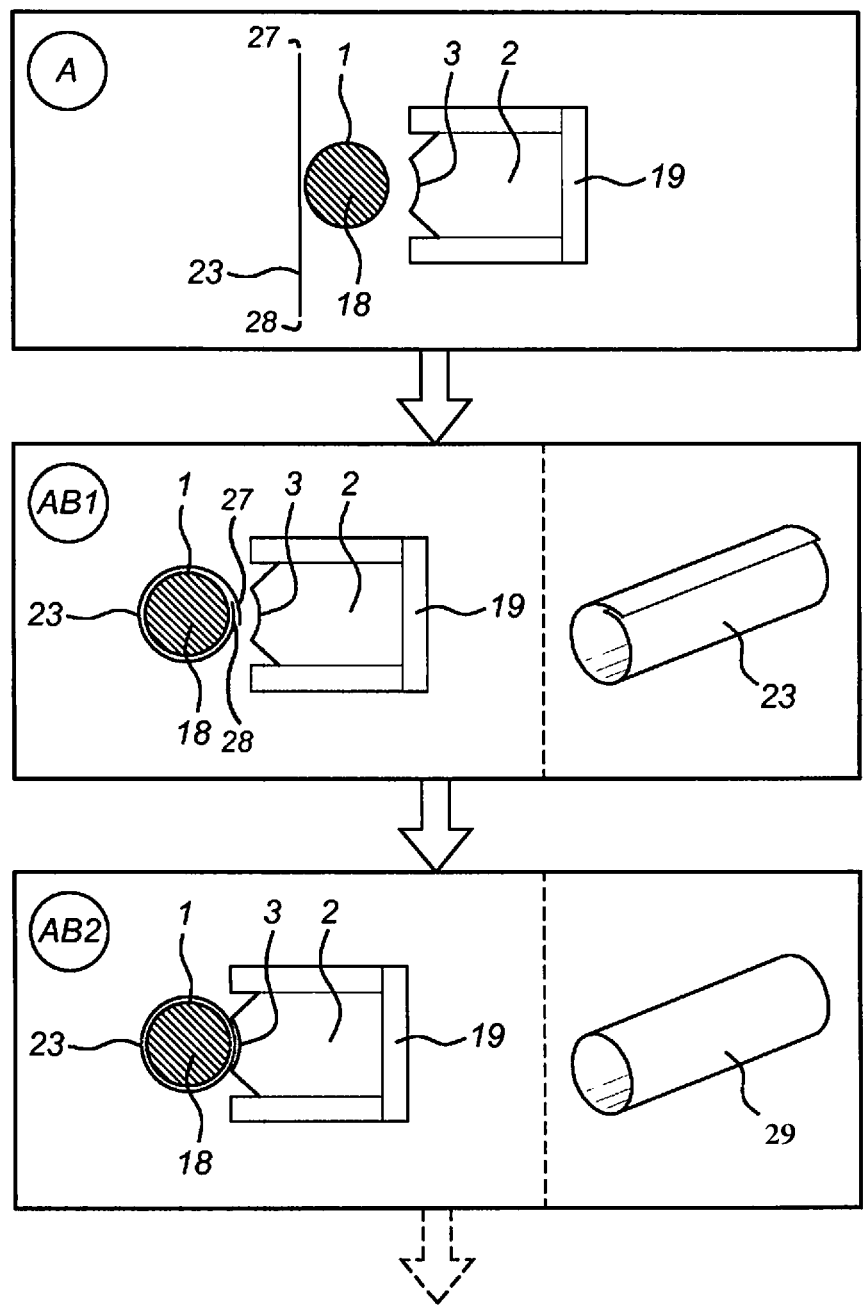
Fig. 4-I

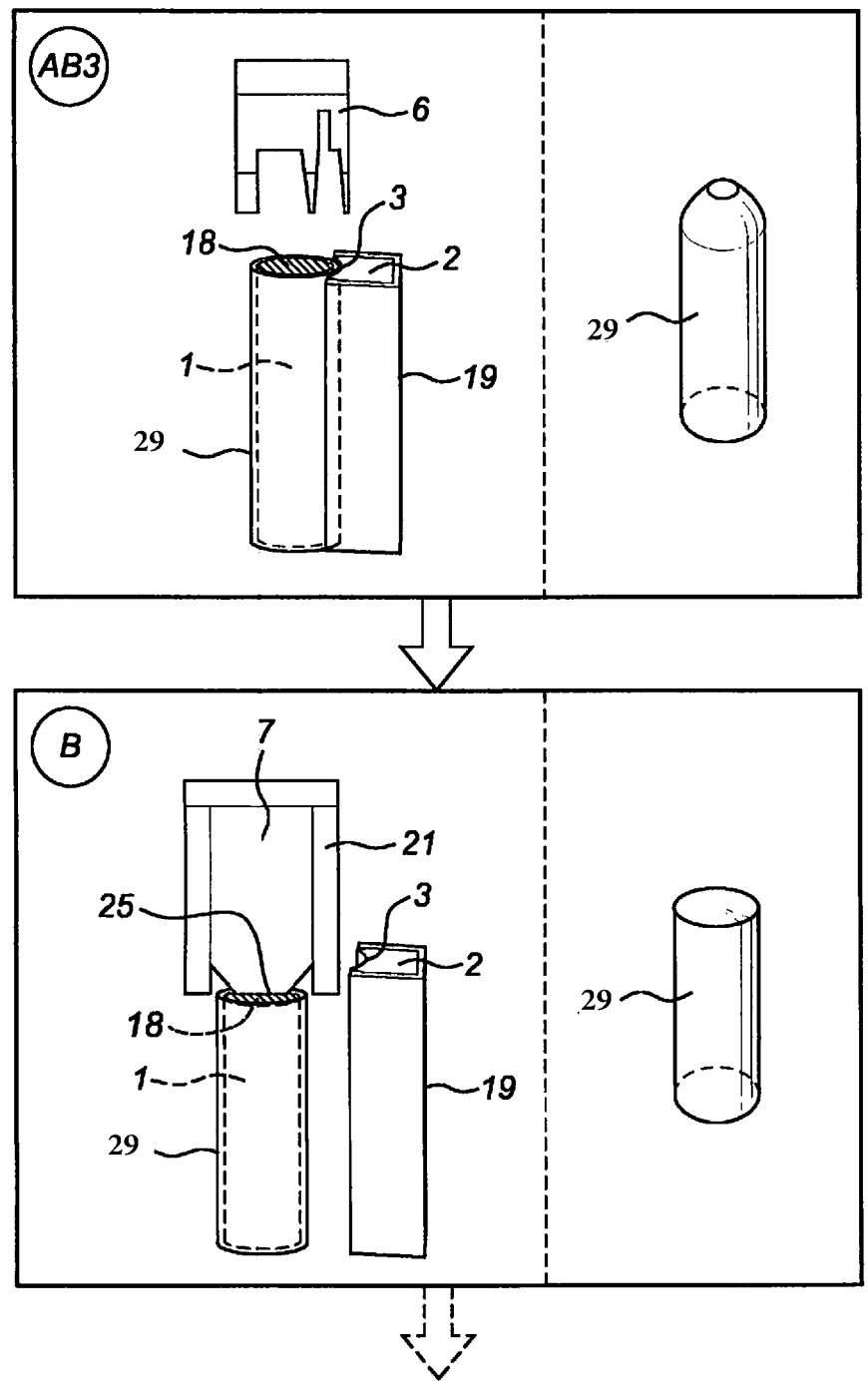
Fig. 4-II

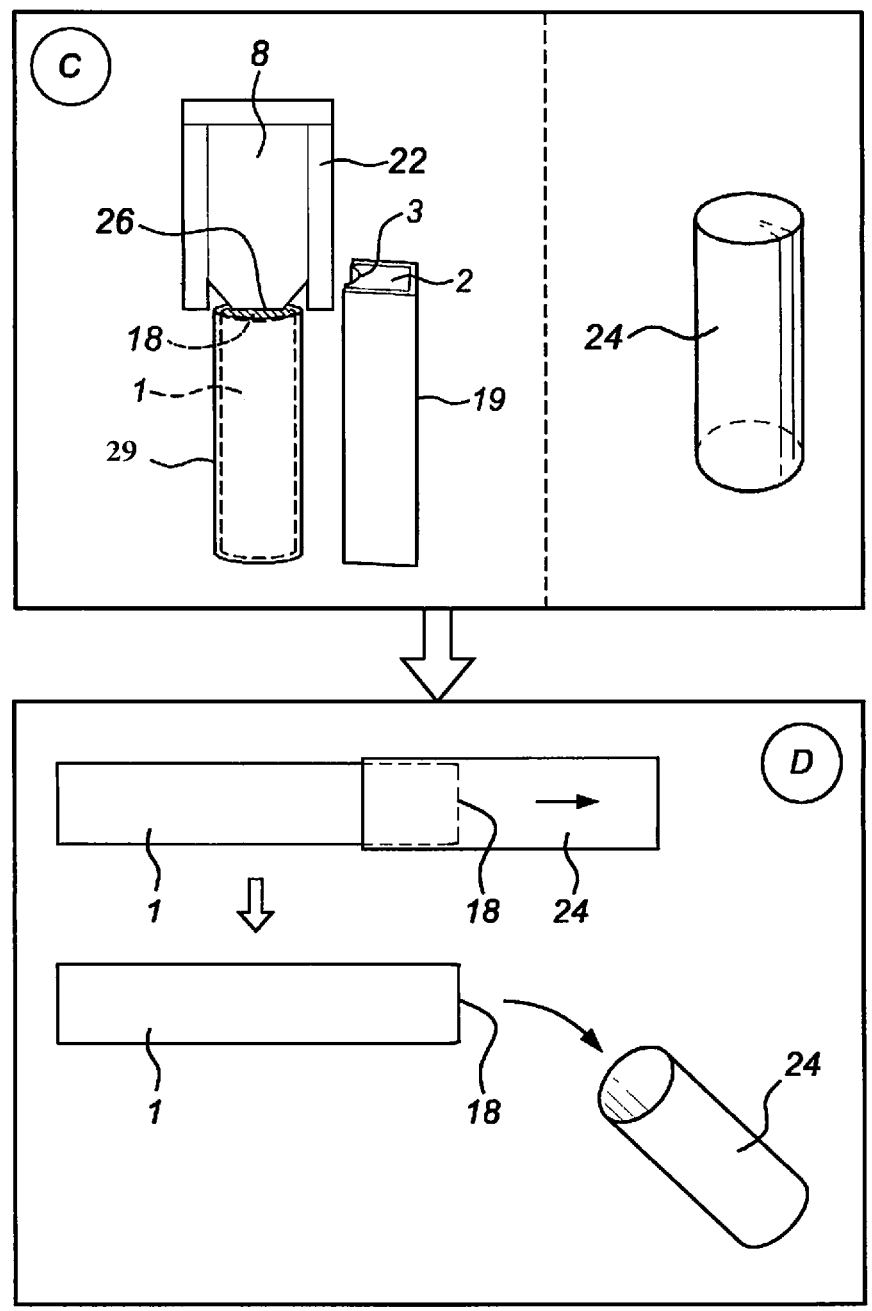
Fig. 4-III

METHOD AND APPARATUS FOR MANUFACTURING A TAMPON PACKAGING

CROSS-REFERENCE TO RELATED APPLICATIONS

This application is the national stage application of corresponding international application number PCT/EP2016/077138, filed Nov. 9, 2016, which claims priority to and the benefit of European application no. 15193734.9, filed Nov. 9, 2015, all of which are hereby incorporated by reference in their entirety.

TECHNICAL FIELD

The invention pertains to the field of manufacturing a tampon packaging and of tampons provided with a tampon packaging. More in particular, the present invention relates to a method and apparatus for manufacturing a tampon packaging wherein the packaging is manufactured separately from the tampon. The present invention thereto also relates to a method and apparatus of forming tubular overwrappings from a heat-sealable material.

BACKGROUND

Tampons are well known in the art and are used for feminine hygiene. Also many tampon manufacturing methods and apparatuses have been disclosed in the prior art. Tampons, and in particular digital tampons, can be covered by a packaging which preferably closely fits the tampon.

Prior art methods for packaging tampons are mainly directed towards immediately packaging the tampon, i.e. the tampon is present during the manufacturing of its packaging. Document EP1477406A1, for instance, discloses such a packaging method, wherein the tampon is inserted inside a tubular folding spindle of constant cross section; a sheet of packing material is then wrapped about the folding spindle and stabilized longitudinally to form a tubular wrapping; the folding spindle and the tubular wrapping, together with the tampon, are then parted; and the two ends of the tubular wrapping are closed transversely about the relative tampon. Heat sealing of tubular packagings are also known from e.g. EP0970888A1 or U.S. Pat. No. 5,533,323A for cellophaning cigarette packets.

However, the present invention relates to another technique, wherein the packaging is manufactured at least partly, and preferably completely, separate from the tampon, i.e. the packaging is essentially manufactured in a suitable form before it is combined with the tampon. Such a method allows for an optimized total production process of packaged tampons. Indeed, if the tampons are packaged directly, the process of forming the tampons and the process of forming the packages need to be performed inline, whereby the total production process speed needs to be optimized taking into account both processes. The present invention allows the production process for the tampon and the production process for the packaging to be at least partly performed in parallel, such that one is capable of optimizing each process separately, thereby also capable of increasing total process speeds.

One prior art process for manufacturing tampon packagings has been developed by Ruggli. Hereby, a strip of thermoplastic film is supplied at the inlet of a wheel to a holding element and then fixed by a staff or rod shaped clamping means. Once the strip is fixed in position the wheel starts to move about 45° around the rotational axis of the wheel. At the first stop the strip is wrapped around the holding means and both of its ends are heat sealed together (forming a "tube"). After another first 45° spin and second 45° spin the outer part of the hull (the one facing away from the center of the wheel) is heat sealed and closed in two distinct second and third heat sealing stations. The cellophane hull (now having a cylindrical body with one open end) is then released at the outlet of the "cellophane wheel" to another wheel were it will be later combined with the tampon.

The problem with the above described packaging method is that the production speed is not high enough to keep up with present-day production speeds of tampon manufacturing apparatuses. As a result, more than one of the prior art tampon packaging manufacturing apparatuses needs to be combined with a tampon manufacturing apparatus in order to increase total production speed. It should be clear that such a solution to increase total production speed is not ideal.

The inventors therefore have found an improved method and apparatus wherein the packaging production speed of the Ruggli method described above can be substantially improved by up to a factor of 2 and even more.

SUMMARY

The present invention concerns a method and apparatus for manufacturing a tampon packaging, as well as a packaged tampon and a system of tampon and packaging.

The inventors have found that in the prior art method described above, a time-consuming step is the stop whereby the strip which has been wrapped around the holding means has both of its ends heat-sealed together (forming a "tube"). In the prior art, this step of heat sealing the strip into a tube is performed during a stop of the conveying means, and can be long because the quality of the heat seal depends on the temperature of the heating element and the duration of the heat-sealing step. More in particular, the quality is improved if heat sealing is performed at lower temperature and for a longer duration.

The inventors have found that performing the heat sealing step during movement of the holding means and of the strip which is wrapped around the holding means leads to an unexpected improvement of the tampon packaging production speed by a factor of up to 2 and more.

Therefore, in a first aspect, the present invention concerns a method for manufacturing a tampon packaging (24), comprising the steps of:

(a) wrapping a strip of heat-sealable film (23) around a holding means (1, 18), whereby a first transversal end (27) of said strip overlaps with a second transversal end (28) of said strip;

(b) heat sealing said first transversal end (27) to said second transversal end (28), thereby forming a tube of film, (c) removing said tube of film from said holding means, thereby obtaining a tampon packaging, characterized in that said heat sealing step (b) is performed at least partly during a combined movement of said holding means (1, 18) and said strip (23).

By performing the heat sealing step of forming a tube of film during movement of the holding means, and of the strip wrapped around it, the time of movement can be used for sealing the transversal ends of the strip together, thereby forming a tube. As a result, no time is lost on a lengthy stop for heat sealing the ends of the strip.

In a preferred embodiment, the present invention provides a method for manufacturing a tampon packaging (24) according to the first aspect of the invention, wherein the method comprises the step of:

(b1) at least partly heat sealing a longitudinal end of said strip (23), said step (b1) being performed after step (a) and before step (c), and before, during or after step (b), thereby obtaining a tube of film with one at least partially closed longitudinal end and one open longitudinal end.

Preferably, said step (b1) is performed during movement of the holding means, thereby again leading to a higher production throughput and/or better quality of heat sealing as the heat sealing is performed during movement of the holding means and does not necessitate a halting of the holding means.

In a preferred embodiment, the present invention provides a method for manufacturing a tampon packaging (24) according to the first aspect of the invention, wherein the method comprises at least one of the steps of:

(a2) creating an underpressure in between the strip of film and the holding means, thereby keeping the wrapped strip of heat-sealable film (23) in place around the holding means, and/or (c2) creating an overpressure in between the tube of film and the holding means, thereby blowing off said tube of film from said holding means for removal, thereby obtaining a tampon packaging.

Herein, preferably the holding means comprise one or more holes in its peripheral surface (1) and/or longitudinal end (18), whereby the holes are in communication with one or more lumen within the holding means, and whereby during step (a2), the underpressure is provided in the one or more lumen and/or whereby during step (b2), the overpressure is provided in the one or more lumen.

In a related aspect, the present invention concerns a tampon packaging manufacturing apparatus comprising a conveying means, which comprises at least one holding means for holding a heat-sealable strip of film wrapped around said holding means, the holding means attached to said conveying means for movement of the holding means in a conveyance direction, and at least one heating element, said holding means and said heating element being movable with respect to each other such that a heat-sealable strip of film wrapped around said holding means can be pressed between said holding means and said heating element and subsequently released, characterized in that said heating element is attached to said conveying means for movement of the heating element in the conveyance direction, and that said heating element is arranged to press and heat-seal a heat-sealable strip of film wrapped around said holding means during movement of said conveying means in said conveyance direction between a first stage and a second stage.

Such an apparatus allows performing the heat-sealing step during movement of the holding means and strip of film wrapped around the holding means. Hereby the heating element is attached to the same conveying means as the holding means and thereby essentially follows the same movement of the holding means in the conveyance direction, thereby allowing to perform the heat sealing step during said movement. Hereby, a relative movement between the heating element and the holding means wrapped with a strip of film can be kept small, typically of a distance such as between 0.1 cm and 5 cm, preferably between 0.2 cm and 4 cm, more preferably between 0.3 cm and 2 cm, such as 0.4 cm, 0.5 cm, 0.6 cm, 0.7 cm, 0.8 cm, 0.9 cm, 1.0 cm, 1.1 cm, 1.2 cm, 1.3 cm, 1.4 cm, 1.5 cm, 1.6 cm, 1.7 cm, 1.8 cm, 1.9 cm, or any value therebetween. In a preferred embodiment, the relative movement can be obtained by pressing the heating element to the holding means provided with the strip. Alternatively or additionally, the relative movement can be obtained by pressing the holding means to the heating element. Thereto, the heating element and/or the holding means are attached to the conveyance means in a moveable manner, preferably at least one of said heating element or said holding means being mounted on the conveyance means by means of a pivoting element and preferably a mechanical or electromechanical actuator.

In a preferred embodiment, the conveying means comprises a rotatable, essentially circular wheel and the conveyance direction is an angular direction around a center axis of said wheel. In a more preferred embodiment, the apparatus comprises a number of holding means for holding a heat-sealable strip of film wrapped around said holding means, each of the holding means attached to said wheel, said number of holding means between 2 and 10, preferably between 4 and 8, most preferably exactly 6, and an equal number of heating elements, each of said heating elements corresponding to one of said holding means. Hereby, each of said holding means and said heating element corresponding with said holding means is movable with respect to each other such that a heat-sealable strip of film wrapped around said holding means can be pressed between said holding means and said corresponding heating element and subsequently released. Each of said heating elements is attached to said wheel, and each of said heating elements is arranged to press and heat-seal a heat-sealable strip of film wrapped around said corresponding holding means during rotation of the wheel between a first stage and a second stage.

In a preferred embodiment, the strip of heat-sealable film is wrapped around a holding means as in step (a) at an inlet of an apparatus which is configured to perform the method for manufacturing a tampon packaging as disclosed herein, preferably an apparatus as disclosed in this document. Hereby, the apparatus comprises an inlet and said holding means of the apparatus are configured to pass the inlet through which a strip can be introduced. A strip can then be introduced at the moment the holding means passes the inlet and is directly wrapped around the holding means. In a preferred embodiment, the apparatus is configured to provide the holding means with a stepwise movement whereby the holding means are halted when they are at or near the inlet. Preferably the holding means are halted during a stage interval, which is preferably at most 2 seconds, more preferably at most 1 second, yet more preferably at most 0.5 s. By wrapping the strip of film around the holding means immediately at the inlet, the heat-sealing step (b) can be started immediately after step (a), thereby allowing more time for performing the heat-sealing step, and thus allowing to increase the quality of the heat-seal.

Also in a preferred embodiment where the heat-sealing step (b1) of the longitudinal end of the strip is performed simultaneously with the heat-sealing step (b) of the overlapping transversal ends of the strip, by wrapping the strip of film around the holding means immediately at the inlet, the heat-sealing steps (b, b1) can be started immediately after step (a), thereby allowing more time for performing the heat-sealing steps (b, b1), and thus allowing to increase the quality of the heat-seal.

In a preferred embodiment of the apparatus, the holding means comprises one or more holes in its peripheral surface (1) and/or longitudinal end (18), whereby the holes are in communication with one or more lumen in the holding means, and whereby the one or more lumen are attachable to one or more pressurizing means, the pressurizing means adapted for creating at different moments in time underpressure and/or overpressure, and whereby the pressurizing means is configurable to provide an underpressure upon wrapping and heat-sealing of a strip and/or to provide an overpressure for removal of the tube.

Note hereby that removal of the tube by creating an overpressure, i.e. by blowing off the tube, turns out to be possible even if the longitudinal end of the tube is not closed, although it tends to be easier if the longitudinal end of the tube is completely closed. Hence preferably, in the embodiments where the tube of film is removed by blowing off the tube of film, the longitudinal end is closed completely. This can be done during step (b1).

This is advantageous, because holding the strip during wrapping and heat-sealing, and removing the heat-sealed strip would otherwise involve moving parts. Moving parts are typically more prone to failure and require a higher level of maintenance than the application of pressure.

The concept of wrapping the strip of heat-sealable film around a holding means at an inlet of an apparatus also leads to reduction of the time it takes to manufacture a tampon packaging, even if a method is used wherein the heat-sealing step (a) is performed when the holding means are halted. Hence, the present invention also concerns a method for manufacturing a tampon packaging, comprising the steps of:

(a1) supplying a strip of heat-sealable film (23) to holding means, preferably via an inlet of an apparatus comprising said holding means (a) wrapping the strip of heat-sealable film (23) around the holding means (1, 18), whereby a first transversal end (27) of said strip overlaps with a second transversal end (28) of said strip;

(b2) subsequently moving said holding means;

(b) heat sealing said first transversal end (27) to said second transversal end (28), thereby forming a tube of film, (c) removing said tube of film from said holding means, thereby obtaining a tampon packaging, characterized in that said wrapping step (a) is performed simultaneously to or immediately after supplying step (a1).

Herein, the supplying and wrapping step are preferably performed when the holding means are halted in a first stop. Further, the heat-sealing step can be performed during a second stop; in this embodiment, the supplying (a1) and wrapping (a) step are performed at a first stop, the holding means are subsequently moved to a second stop (step (b2)), where the heat-sealing step (b) is performed. However, in a preferred embodiment, the heat-sealing step (b) is performed at least partially during said moving step (b2), as further described in this document. In a preferred embodiment, a longitudinal end of said strip (23) is at least partly heat-sealed (step (b1)) during step (b), thereby obtaining a tube of film with one at least partially closed, and preferably completely closed, longitudinal end, and one open longitudinal end.

In a further aspect, the present invention concerns a tampon provided with a packaging according to the present invention and a system of tampon and tampon packaging according to the present invention.

There are currently two types of tampons. The first type is a digitally insertable tampon which is designed to be inserted directly by the user's fingers. The second type is an applicator style tampon which is designed to be inserted with the aid of an applicator. Both types of tampons can be used in the present invention, although a digital tampon is preferred. Both types are usually made by folding or rolling rectangular strips of absorbent material into a blank and then compressing the blank into a cylindrically-shaped pledget. Both folding or rolling of the strips can be used to manufacture a tampon for the present invention. However, preferably the tampon of the present invention is made by rolling the absorbent material into a blank and compressing the blank into a pledget of essentially cylindrical shape.

In yet a further aspect, the present invention concerns a method for manufacturing a packaged tampon, comprising the steps of:

providing a tampon;

manufacturing a tube-like tampon packaging according to the present invention, said tampon packaging comprising at least one open longitudinal end and preferably one at least partially closed longitudinal end, more preferably said at least partially closed longitudinal end being completely closed;

combining said tampon packaging with said tampon by:
  inserting said tampon into said tampon packaging via said open longitudinal end, or
  sliding said tampon packaging via said open longitudinal end over said tampon;

optionally subsequently at least partially, preferably completely, closing said open end, preferably by heat sealing, thereby obtaining a packaged tampon.

DESCRIPTION OF FIGURES

FIG. 4-I shows a schematically presented embodiment for steps A, AB1, and AB2 of the manufacturing of a tampon packaging 24. FIG. 4-II shows a schematically presented embodiment for steps AB3 and B of the manufacturing of a tampon packaging 24. FIG. 4-III shows a schematically presented embodiment for steps C and D of the manufacturing of a tampon packaging 24.

DETAILED DESCRIPTION OF THE INVENTION

Figure 1:
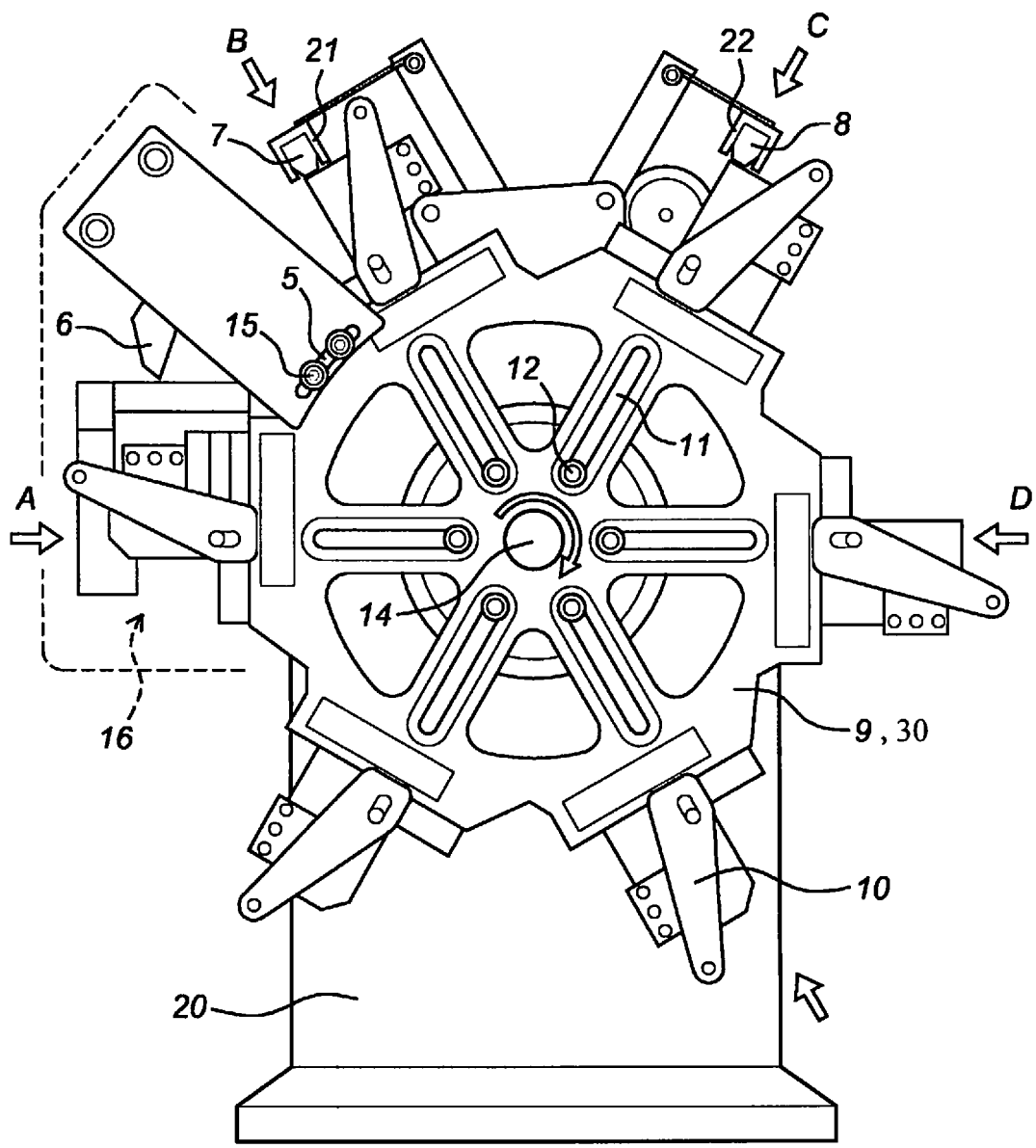
FIG. 1 shows an embodiment of a tampon packaging manufacturing apparatus according to the present invention.

The invention is further described with references to the figures.

In a first aspect, the present invention concerns a method for manufacturing a tampon packaging 24, comprising the steps of:
- (a) wrapping a strip of heat-sealable film 23 around a holding means 1, 18, whereby a first transversal end 27 of said strip overlaps with a second transversal end 28 of said strip;
- (b) heat sealing said first transversal end 27 to said second transversal end 28, thereby forming a tube of film,
- (c) removing said tube of film from said holding means, thereby obtaining a tampon packaging 24, wherein said heat sealing step (b) is performed at least partly during a combined movement of said holding means 1, 18 and said strip 23.

Heat sealing of a heat-sealable film 23 is a time-consuming step during the production of a tampon packaging 24. The tampon packaging 24 production processes as known from the state of the art perform this heat sealing in a stationary fashion. The present invention, on the contrary, performs the heat sealing step at least partly during a combined movement of said holding means 1, 18 and said strip of heat-sealable film 23, thereby substantially increasing the production rate of tampon packaging 24 and the quality of the heat-seal.

This solution is not to be regarded as obvious for a person skilled in the art. Such person would rather try to limit the time of the heat sealing step by altering materials and/or production parameters, which unavoidably leads to high investments in time and equipment. For instance, one could increase the temperature at which the heat sealing step is performed. This would lead to a reduced time for heat-sealing, but would lead to inferior quality of the heat-seal. Furthermore, the temperature for heat-sealing the heat-sealable film is limited by the material properties of the film, hence also the time gain by increasing the temperature for the heat-sealing step is limited.

The solution of the present invention, on the other hand, increases the production rate of tampon packaging 24 with minimal efforts, constant requirements for space and increased quality.

Said holding means 1, 18 preferably comprises a peripheral surface 1, said strip 23 preferably being wrapped in a close fit around the peripheral surface 1. In a particularly preferred embodiment, the holding means comprises a substantially cylindrical holding rod. In a preferred embodiment, the strip 23 is wrapped around the holding rod such that a longitudinal end of the wrapped strip extends beyond a longitudinal end of the holding rod. This allows folding of said longitudinal end of the wrapped strip or tube over said longitudinal end of the holding rod for a heat-sealing of the longitudinal end of the strip or tube in a subsequent step (b1), thereby at least partly, and preferably completely, closing said longitudinal end of the strip or tube.

In a preferred embodiment, the present invention provides a method for manufacturing a tampon packaging 24 according to the first aspect of the invention, wherein the method comprises the step of:
(b1) at least partly heat sealing a longitudinal end of said strip 23, said step (b1) being performed after step (a) and before step (c), and before, during or after step (b), thereby obtaining a tube of film with one at least partially closed longitudinal end and one open longitudinal end.

In an embodiment, said step (b1) is performed when the holding means are halted. Preferably, said step (b1) is performed during movement of the holding means, thereby again leading to a higher production throughput and/or better quality of heat sealing as the heat sealing is performed during movement of the holding means and does not necessitate a halting of the holding means.

In a preferred embodiment, the present invention provides a method for manufacturing a tampon packaging 24 according to the first aspect of the invention, wherein prior to step (b1), said longitudinal end of said strip 23 is folded at least partly inwards, preferably by folding said longitudinal end of said strip over a longitudinal end of said holding means 1, 18.

In a preferred embodiment, the present invention provides a method for manufacturing a tampon packaging 24 according to the first aspect of the invention, wherein said holding means 1, 18 and said strip are at least partly moving rotationally during said heating step b.

In a preferred embodiment, the present invention provides a method for manufacturing a tampon packaging 24 according to the first aspect of the invention, wherein said holding means 1, 18 is attached to a conveying means 30 for moving said holding means, preferably whereby said conveying means 30 is moving rotationally.

In a preferred embodiment, the present invention provides a method for manufacturing a tampon packaging 24 according to the first aspect of the invention, comprising the step of:
(a1) supplying said strip of film 23 to said holding means 1, 18 via an inlet of said conveying means 30, prior to said heat-sealing step (b) and optionally prior to a heat-sealing step (b1) for at least partly heat sealing a longitudinal end of said strip 23, preferably wherein said supplying step (a1) is performed at least partly simultaneously with said wrapping step (a).

Preferably, said heat sealing step (b1) for heat sealing the open longitudinal end is conducted at least partly without interrupting the movement of said conveying means 30.

In a preferred embodiment, the present invention provides a method for manufacturing a tampon packaging 24 according to the first aspect of the invention, comprising the step of:
(c1) conveying said heat-sealed tube of film to an outlet of said conveying means 30, preferably wherein conveying step (c1) is performed prior to said removing step (c).

In a preferred embodiment, the present invention provides a method for manufacturing a tampon packaging 24 according to the first aspect of the invention, wherein said strip of heat-sealable film comprises a longitudinal dimension of between 3 cm and 25 cm, preferably between 5 cm and 20 cm, more preferably between 6 cm and 15 cm, such as 6 cm, 7 cm, 8 cm, 9 cm, 10 cm, 11 cm, 12 cm, 13 cm, 14 cm, 15 cm or any value there between, and/or wherein said strip of heat-sealable film comprises a transversal dimension of between 1.5 cm and 7.5 cm, preferably between 2.0 cm and 6.0 cm, more preferably between 2.5 cm and 5.0 cm, such as 2.5 cm, 2.8 cm, 3.0 cm, 3.2 cm, 3.5 cm, 3.8 cm, 4.0 cm, 4.2 cm, 4.5 cm, 4.8 cm, 5.0 cm or any value there between.

In an embodiment, the present invention provides a method for manufacturing a tampon packaging 24 according to the first aspect of the invention, wherein said heat sealing step (b1) for heat sealing the open longitudinal end is conducted at least two times.

In a preferred embodiment, the present invention provides a method for manufacturing a tampon packaging 24 according to the first aspect of the invention, wherein said strip of film 23 is a thermoplastic material.

In a preferred embodiment, the present invention provides a method for manufacturing a tampon packaging 24 according to the first aspect of the invention, whereby said strip of film comprises cellulose, preferably regenerated cellulose, more preferably said strip of film comprising cellophane.

In a preferred embodiment, the present invention provides a method for manufacturing a tampon packaging 24 according to the first aspect of the invention, wherein said strip of film 23 is a heat-shrinkable material. With a heat-shrinkable material, it becomes possible to manufacture the packaging slightly larger than the tampon, thereby allowing easy insertion of the tampon into the packaging in a later step, and subsequently heat the tampon packaging provided with the tampon to tighten the packaging around the tampon.

In a preferred embodiment, the present invention provides a method for manufacturing a tampon packaging 24 according to the first aspect of the invention, wherein said heat sealing step (b) is conducted with a heating element 2 which is moving along with said holding means 1, 18.

In a preferred embodiment, the present invention provides a method for manufacturing a tampon packaging 24 according to the first aspect of the invention, wherein said heat sealing step (b) is conducted with a heating element 2 with a concave surface 3, whereby said concave surface 3 is contacting and providing heat to the strip 23 or tube of film 29. This is particularly preferred if the holding means comprises a convex peripheral surface, preferably whereby the holding means comprises a substantially cylindrical holding rod. In such an embodiment, the convex peripheral surface and the concave surface of the heating element preferably closely fit each other in order to provide heat to the wrapped strip of film or tube of film over a wider area. In an embodiment, said optional step (b1) is conducted with a heating element with a concave surface whereby said concave surface is contacting and providing heat to the strip 23 or tube of film 29. In a more preferred embodiment, however, said optional step (b1) is conducted with a heating element 7, 8 with an essentially flat surface 25, 26, whereby said flat surface is contacting and providing heat to the strip 23 or tube of film 29.

In an embodiment of the apparatus of the present invention, the apparatus comprises a top heating element which is attached to said conveying means for movement of the top heating element in the conveyance direction, and that said top heating element is arranged to press and heat-seal a longitudinal end of a strip of film wrapped around said holding means during movement of said conveying means in said conveyance direction. Preferably said top heating element and the heating element are thermally connected or form an integral top-and-side heating element. This ensures that essentially the same temperature is used for heat-sealing both the longitudinal end as the peripheral side of the tube, and in case they form an integral top-and-side heating element, that the heat-sealing of the longitudinal end and the peripheral side of the tube is performed for essentially the same period.

In a preferred embodiment, the present invention provides a method for manufacturing a tampon packaging 24 according to the first aspect of the invention, whereby said holding means does not comprise a tampon, thereby manufacturing a tampon packaging 24 separate from a tampon.

In an embodiment, said heating step (b) comprises pressing a heating element at a heating temperature against the wrapped strip of film in an overlap region of the first transversal end and second transversal end.

The term "heating temperature" within this document relates to a temperature which is sufficient to heat-seal the strip, without disintegrating or burning the strip.

The heating temperature of the heat sealing element can be adjusted in sight of the speed of the holding means and/or of the conveying means onto which the holding means can be mounted. In case of a higher speed, the time until the heat sealing element would disconnect from the holding means shortens accordingly, i.e. the duration of the heat sealing decreases accordingly. Therefore it is necessary to increase the temperature in order to ensure a proper sealing of the two ends of the strip of film. In an embodiment, said heating temperature can be set taking into account said speed of the holding means and/or the conveying means. The heating temperature can be constant, stepwise constant, or can follow a temperature profile, i.e. the heating temperature may be variable. The following problems can be addressed accordingly:

Depending on the material the temperature cannot exceed a specific temperature as otherwise the material would disintegrate/burn. Hence, in an embodiment, the heating temperature is lower than a maximum temperature, which is pre-determined taking into account the material properties of the film.

Depending on the material the shut-down and start-up procedure can lead to inadequate temperature levels given the speed of the machine. This may lead to the heating elements to collect some residue of molten and later burned film. Hence, in an embodiment, the heating temperature follows a temperature profile, which preferably varies during a shut-down procedure and/or a start-up procedure of the method or apparatus according to the present invention, while also preferably remaining essentially constant or stepwise constant between said start-up and shut-down procedures.

In view of the problems given above, it can also be preferred to include a, preferably automated, temperature control means that will adjust the temperature of the heating element in accordance to the speed of the holding means and/or conveying means, in particular in accordance with the rotational speed of the holding means and/or conveying means in an embodiment where the holding means are following a rotational path between the wrapping step and the removing step, e.g. when the holding means are mounted on a rotatable wheel.

Furthermore, in an embodiment, the temperature of the heating elements follow a temperature profile which comprises reaching a heating temperature during said heat-sealing step (b), and which comprises reaching a wait temperature, which is lower than said heating temperature, during a period in between consecutive steps (b) which are being performed by pressing said heating element to said strip of film wrapped around the holding means. Such a temperature profile allows to save energy.

In a preferred embodiment, said heating step (b) comprises heat-sealing said first transversal end 27 to said second transversal end 28, thereby forming a tube of film, for a pre-determined duration and/or for a pre-determined distance along a conveyance direction defined by said combined movement of wrapped strip of film and holding means. This is preferably done by pressing a heating element at a heating temperature against the wrapped strip of film in an overlap region of the first transversal end and second transversal end for said pre-determined duration and/or said pre-determined distance, and subsequently disconnecting the heating element from the film. Hereby, the heat sealing can be performed for said duration by placing a release console for indicating that the heating element is to be disconnected from the film, at a release location along said combined movement of wrapped strip of film and holding means, said release location being determined taking into account a speed of said combined movement and said pre-determined duration, i.e. the release location can be determined as the location which the holding means and the wrapped film reach after said pre-determined duration. Hence, an apparatus according to the present invention preferably comprises a release console at a release location as disclosed above.

Preferably, said combined movement is a rotational movement and the conveyance direction is a rotational direction.

In a preferred embodiment, the present invention provides a method for manufacturing a tampon packaging (24) according to the first aspect of the invention, wherein the method comprises at least one of the steps of:

(a2) creating an underpressure in between the strip of film and the holding means, thereby keeping the wrapped strip of heat-sealable film (23) in place around the holding means, and/or (c2) creating an overpressure in between the tube of film and the holding means, thereby blowing off said tube of film from said holding means for removal, thereby obtaining a tampon packaging.

Herein, preferably the holding means comprises one or more holes in its peripheral surface (1) and/or longitudinal end (18), whereby the holes are in communication with one or more lumen within the holding means, and whereby during step (a2), the underpressure is provided in the one or more lumen and/or whereby during step (b2), the overpressure is provided in the one or more lumen. Note that step (a2) is preferably performed from before or during wrapping step (a), and preferably the underpressure is provided during steps (b), (b1) and/or (b2) until just before removal step (c), and that step (c2) is preferably performed at least during step (c).

In a second aspect, the present invention concerns a method for manufacturing a packaged tampon, comprising the steps of:

providing a tampon;

manufacturing a tube-like tampon packaging according to the first aspect of the present invention, said tampon packaging comprising at least one open longitudinal end and preferably one at least partially closed longitudinal end; combining said tampon packaging with said tampon by:

inserting said tampon into said tampon packaging via said open longitudinal end, or sliding said tampon packaging via said open longitudinal end over said tampon;

optionally subsequently at least partially closing said open end, preferably by heat sealing, thereby obtaining a packaged tampon.

In a preferred embodiment, the present invention provides a method for manufacturing a packaged tampon according to the second aspect of the invention, wherein the step of combining the tampon packaging 24 with the tampon is performed after or during step (c) of removing the tampon packaging from the holding means 1, 18.

In a preferred embodiment, the tampon packaging comprises, and preferably consists solely of, heat-shrinkable material, and the method comprises the step of:

after combining the tampon and the tampon packaging, heating the tampon packaging to tighten the packaging around the tampon.

In a third aspect, the present invention concerns a system comprising a tampon and a tampon packaging manufactured according to the first aspect of the present invention, said tampon packaging arranged to closely fit over said tampon.

In an embodiment, of the present invention, the packaging is manufactured slightly larger than the tampon which is intended to be inserted therein. Preferably, said tampon packaging comprises a diameter which is at most 20% larger than the diameter of the tampon, more preferably at most 15%, still more preferably at most 10%, yet more preferably at most 5% larger than the diameter of the tampon and/or said tampon packaging comprises a diameter which is at least 0.5% larger than the diameter of the tampon, more preferably at least 1% larger than the diameter of the tampon.

In a fourth aspect, the present invention concerns a tampon provided with a tampon packaging 24 manufactured according to the first aspect of the present invention.

In a fifth aspect, the present invention concerns a tampon packaging manufacturing apparatus arranged for manufacturing a tampon packaging 24 using a method according to the first aspect of the present invention.

In a sixth aspect, the present invention concerns a tampon packaging manufacturing apparatus comprising a conveying means, which comprises at least one holding means for holding a heat-sealable strip of film wrapped around said holding means, the holding means attached to said conveying means for movement of the holding means in a conveyance direction, and at least one heating element, said holding means and said heating element being movable with respect to each other such that a heat-sealable strip of film wrapped around said holding means can be pressed between said holding means and said heating element and subsequently released, wherein said heating element is attached to said conveying means for movement of the heating element in the conveyance direction, and that said heating element is arranged to press and heat-seal a heat-sealable strip of film wrapped around said holding means during movement of said conveying means in said conveyance direction.

In a preferred embodiment, said apparatus comprises supplying means for supplying a strip of film to said holding means. In a preferred embodiment, said apparatus comprises an actuator which is arranged to actuate both the supplying means and the conveying means, said actuator preferably being arranged to cause a discontinuous movement, i.e. a repeated stop-and-go movement, to said conveyance means. More preferably said actuator comprises a Geneva drive. Hereby, the conveying means are arranged to halt while the strip of film is supplied to, and preferably also wrapped around, the holding means.

In a preferred embodiment of the apparatus, the holding means comprises one or more holes in its peripheral surface (1) and/or longitudinal end (18), whereby the holes are in communication with one or more lumen, and whereby the one or more lumen are attachable to one or more pressurizing means, the pressurizing means adapted for creating at different moments in time underpressure and/or overpressure, whereby the pressurizing means is configurable to provide an underpressure upon wrapping and heat-sealing of a strip and/or to provide an overpressure for removal of the tube.

This is advantageous, because holding the strip during wrapping and heat-sealing, and removing the heat-sealed strip would otherwise involve moving parts. Moving parts are typically more prone to failure and require a higher level of maintenance than the application of pressure.

The present invention is further disclosed in the following examples with reference to the figures which illustrate specific embodiments of the methods, systems, devices and apparatuses according to the invention. The examples should be interpreted as illustrative. However, the examples should not be interpreted as limitative.

Example 1

Figure 2:
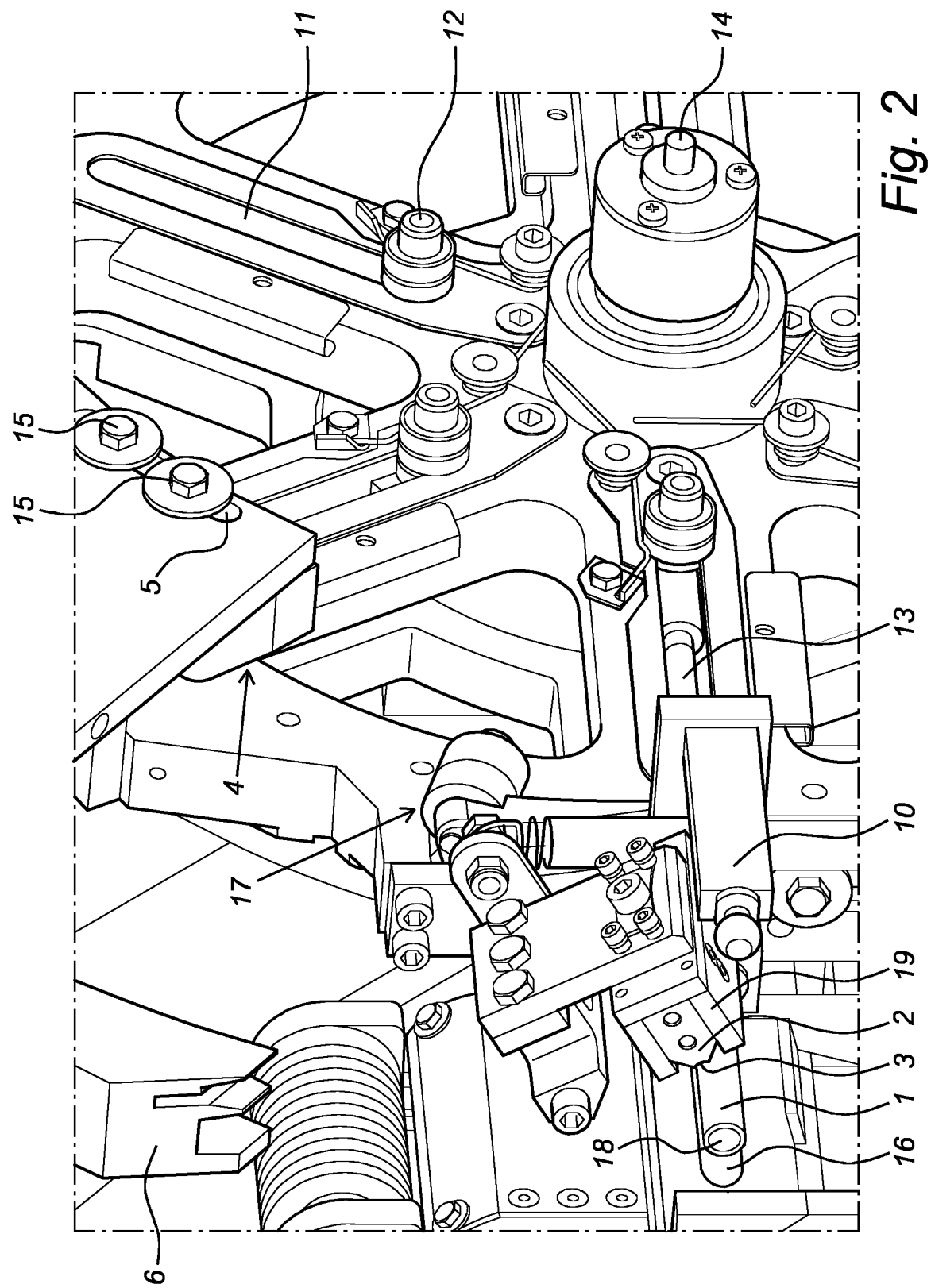
FIG. 2 shows a detailed view of an embodiment of the tampon packaging manufacturing apparatus according to the present invention.
Figure 3:
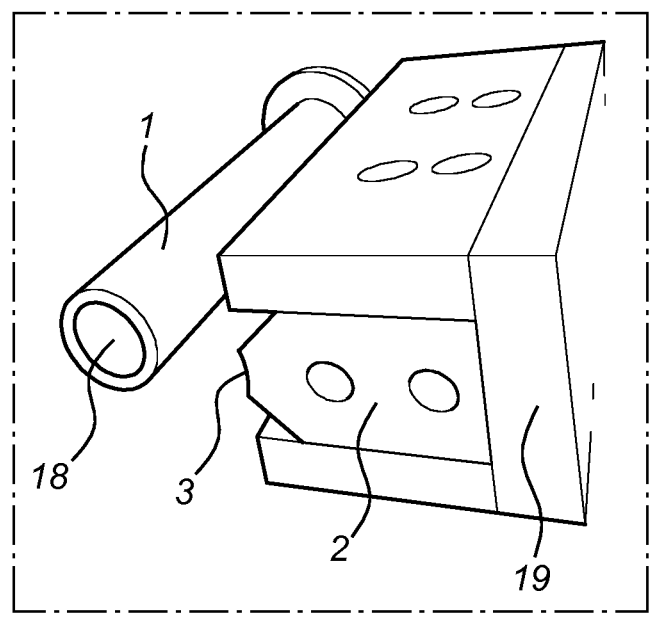
FIG. 3 shows an embodiment of a system comprising holding means and a heating element according to the present invention.

FIG. 1 shows an embodiment of a tampon packaging manufacturing apparatus according to the present invention. FIG. 2 shows a detailed view of an embodiment of the tampon packaging manufacturing apparatus according to the present invention. FIG. 3 shows an embodiment of a system comprising holding means and a heating element according to the present invention. FIGS. 4-I, 4-II and 4-III show a schematically presented embodiment for the manufacturing of a tampon packaging 24.

The apparatus comprises a conveyance means in the form of a wheel (9) which rotates clockwise during operation around an axis (14). The movement of the wheel is a stepwise clockwise rotation, whereby the rotational movement is halted every 60°. Six holding means (1, 18) and six corresponding heating elements (2) are mounted on the wheel (9) and follow the same stepwise rotational movement. The holding means comprise a top side (18) and an essentially cylindrical peripheral side (1). When a holding means (1, 18) arrives at position A, the rotation is halted and a strip of film is supplied to the holding means, using a film delivery means (16). The strip is immediately wrapped around the peripheral side (1) of the holding means with the first transversal end (27) and the second transversal end (28) overlapping at the side of the heating element (2) (see also FIG. 4-I, position A and AB1). The heating element (2) is pushed with a concave surface (3) against the peripheral side (1) of the holding means, thereby clamping the film in its position around the holding means and preferably also immediately heat-sealing the strip of film.

The holding means around which the strip of film is wrapped in position A are then rotated towards position B, while the heating element performs the heat sealing step (b). During said movement from A to B, the film which is preferably already partly sealed into a tube of film encounters a claw (6) which comprises a narrowing slit, i.e. a slit which narrows in a radial direction away from the axis (14) and preferably which narrows in a clockwise angular direction, through which slit a longitudinal end of the wrapped strip or tube of film can be folded inwards. The wrapped strip or tube of film hereby can be folded over the top (18) of the holding means.

In order to arrange for said longitudinal end of the wrapped film or tube of strip to extend beyond the tip (18) of the holding means, the holding means may be mounted on the wheel via an extendable bar (13). Said extendable bar can extend or retract radially with respect to the axis (14), thereby also changing the radial position of the holding means and/or changing the position of the wrapped strip or tube of film with respect to the top of the holding means (18) by effectively sliding the film radially over the peripheral side of the holding means (1). The radial position of the extendable bar (13) can be further arranged via e.g. bolting means (12) mounting the extendable bar to a slit (11) in an arm (10) of the wheel.

The claw (6) is stationary with respect to the wheel, i.e. it can be mounted on a frame (20) which also supports the rotatable wheel (9).

In the present case, a release console (4) is also mounted stationary on the apparatus by bolting means (15) in an arc-shaped slit, allowing its position to be re-arranged along the movement of the holding means. At a certain moment during the movement of the wheel, a contacting element (17) which is mounted on the wheel and is functionally connected to the heating element, contacts the release console (4) and induces the heating element (2) to move away from the peripheral side (1) of the holding means. This contact can be mechanically or can be e.g. electromagnetically. By appropriate positioning of the release console (4), the time of the heat-sealing step can be manipulated for a certain angular speed of the wheel (9). Preferably the release control is arranged between the position of supplying and/or wrapping the strip of film around the holding means and the position of the first top heat sealing element. However, the release control may be positioned further towards the removing position (position D in the present example) in order to increase the time of the heat-sealing step for heat sealing the strip of film into a tube of film.

The holding means with the at least partly heat-sealed tube of film then reaches position B, when the wheel is halted again. During the halting of the wheel, the holding means and the tube of film which are at position B, undergo a heat-sealing of the longitudinal end which by a first, stationary positioned, top heating element (7) which is pushed against the inwards folded longitudinal end of the tube of film.

Subsequently, the wheel is rotated another 60° and the tube of film with a partly closed longitudinal end is moved to and halted in position C, where a second, stationary positioned, top heating element (8) is pushed against the already partly closed longitudinal end of the tube in order to close it completely, thus forming a half-closed tubular tampon packaging.

In a last step, the half-closed tubular packaging is moved to and halted in position D, where the packaging is removed from the holding means, e.g. by a radially expansive movement of the extendable bar (13) which pushes the packaging into a packaging grasping means which is arranged to grasp the packaging and provide it to a further downstream process where the packaging is combined with a tampon and preferably also completely sealed.

Note that all heating elements can be provided with insulating elements (19, 21, 22).

A process according to the invention is also illustrated in FIGS. 4-I, 4-II and 4-III. At position A, a strip of film (23) with longitudinal ends (27, 28) is supplied to a holding means (1, 18). A heating element (2) with a concave surface (3) corresponding to a peripheral side (1) of the holding means, and an insulating element (19) is positioned at a certain distance from the holding means. The strip of film is wrapped around the peripheral side (1) of the holding means in step AB1, whereby the longitudinal ends (27, 28) overlap at the side of the heating element. The wrapped strip of film has a tubular form (23), but the longitudinal ends have not yet been heat-sealed. The heat sealing is performed in AB2, which is preferably performed during combined movement of the holding means, the film wrapped around the holding means and the heating element. A tube of film (23) is thus being formed.

Optionally, in a step AB3, the holding means, the tube of film and the heating element encounter a claw (6). In order for the claw to fold the longitudinal end of the tube of film inwards, the heating element can be released from the strip and the holding means can be partially retracted from the tube of film.

Then, in step B, a first top heat-sealing element (7) is pushed with an essentially flat surface (25) against the longitudinal end of the tube of film. In a further step C, a second top-heat-sealing step with a second top heat-sealing element (8) can be performed to completely close off one longitudinal end of the packaging (24). The packaging (24) is subsequently removed from the holding means in a step D. It can be typically combined with a tampon in a downstream process. In the present case, wherein an essentially flat surface is used to close off one longitudinal end, a tampon is preferably inserted with its withdrawal end first into the packaging's remaining open longitudinal end and is subsequently closed off at the side of the insertion end of the tampon, thereby completely sealing the packaging, preferably also by heat-sealing.

The apparatus shown in FIG. 1 comprises 6 holding means and six corresponding heating elements, and is configured to halt after every rotation of 60°. However, it is clear that another number of holding means can be provided. The number of holding means is, however, preferably kept to at most 8, more preferably at most 6.

Example 2

FIGS. 5A, 5B, 5C, 5D and 5E show a schematically presented preferred embodiment for the manufacturing of a tampon packaging. In this embodiment, a longitudinal end of the strip is heat-sealed (b1) simultaneously with the heat-sealing step (b) of the overlapping first and second transversal ends (27, 28) of the strip. This simultaneous heat-sealing (b, b1) occurs in a preferred embodiment of the present invention during movement of the holding means (1, 18) and the heating element (2, 3) along the conveyance direction. This conveyance direction can be determined by rotation of a wheel onto which the holding means (1, 18) and the heating element (2, 3) are attached. These attachments can optionally be in a movable manner with respect to the wheel, as to allow the concave surface (3) of the heating element (2) and the peripheral surface (1) of the essentially cylindrical holding means (1, 18) to come into contact or near contact.

Figure 5A:
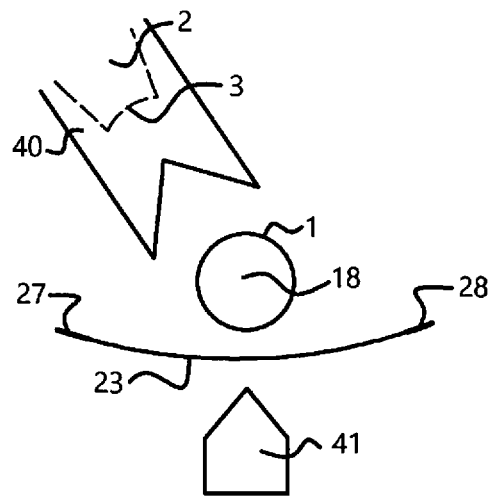
FIG. 5A shows a schematically presented alternative embodiment for a step in the manufacturing of a tampon packaging.
Figure 5B:
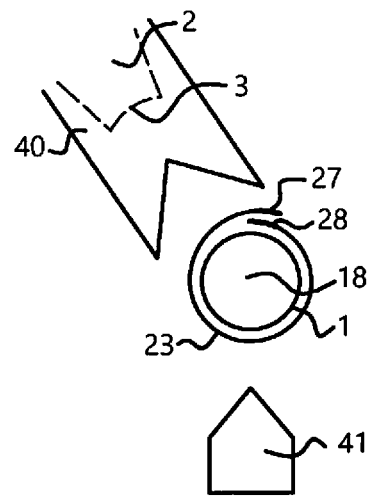
FIG. 5B shows a schematically presented alternative embodiment for a step in the manufacturing of a tampon packaging.
Figure 5C:
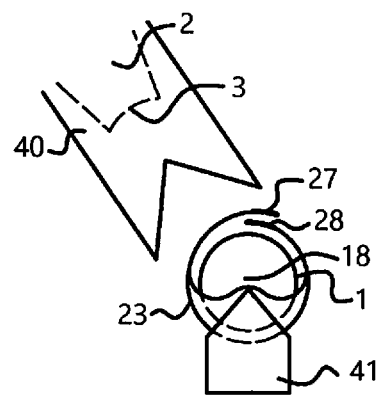
FIG. 5C shows a schematically presented alternative embodiment for a step in the manufacturing of a tampon packaging.
Figure 5D:
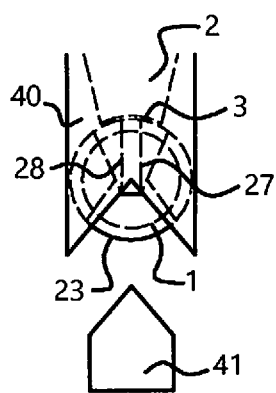
FIG. 5D shows a schematically presented alternative embodiment for a step in the manufacturing of a tampon packaging.
Figure 5E:
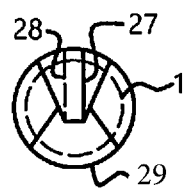
FIG. 5E shows a schematically presented alternative embodiment for a step in the manufacturing of a tampon packaging.

In FIG. 5A an essentially rectangular strip (23) is provided. Preferably, this strip comprises a thermoplastic material such as cellophane. The strip comprises a first transversal end (27) and a second transversal end (28). In FIG. 5B, the strip is wrapped around peripheral surface (1) of the holding means (1, 18), whereby the strip extends in the longitudinal direction beyond the flat surface (18) at the front longitudinal end of the essentially cylindrical holding means (1, 18). The transversal ends (27, 28) are thereby positioned to form an overlapping region along the entire longitudinal direction of the cylindrical holding means (1, 18). The wrapped strip is held in place by means of one or more holes in the peripheral surface (1) of the holding means (1, 18) through which an underpressure with respect to the environment is exerted upon the strip. In FIG. 5C, a first folding element (41) folds a part of the strip onto the flat surface (18) at the front longitudinal end of the cylindrical holding means (1, 18). Subsequently, in FIG. 5D, a second folding element (40) folds the remaining piece of strip extending beyond the cylindrical holding means (1, 18) onto the flat surface (18) at the front longitudinal end of the cylindrical holding means (1, 18). Thereby multiple plies can be applied in the strip. The folded longitudinal end of the strip is held in place by means of one or more holes in the flat surface (18) at the front longitudinal end of the cylindrical holding means (1, 18) through which an underpressure with respect to the environment is exerted on the strip.

The second folding element (40) also comprises a top heat-sealing element and a longitudinal heat-sealing element (2) with a concave surface (3). The concave surface (3) matches the shape and curvature of the peripheral surface (1) of the cylindrical holding means (1, 18), and can be brought in near perfect contact with the peripheral surface (1) of the cylindrical holding means (1, 18) and/or can press the strip (23) in near perfect contact with both the peripheral surface (1) of the cylindrical holding means (1, 18) and the concave surface (3) of the longitudinal heat-sealing element (2). The top heat-sealing element and the longitudinal heat-sealing element (2, 3) simultaneously heat-seal the overlapping transversal ends (27, 28) of the strip in the longitudinal direction and the folded longitudinal end of the strip which is folded onto the flat surface (18) of the top longitudinal end of the cylindrical holding means (1, 18). Thereby a tubular tampon packaging or hull is formed with one sealed longitudinal end and one open longitudinal end. The hull is removed from the holding means (1, 18) by means of one or more holes in the peripheral surface (1) and/or one or more holes in the flat surface (18) at the front longitudinal end of the holding means (1, 18) through which an overpressure with respect to the environment is exerted on the hull. The sealed longitudinal end is schematically presented in FIG. 5E.

The invention claimed is:

1. Method for manufacturing a tampon packaging (24), comprising the steps of:
   (a) wrapping a strip of heat-sealable film (23) around a holding means (1, 18), whereby a first transversal end (27) of said strip overlaps with a second transversal end (28) of said strip;
   (b) heat sealing said first transversal end (27) to said second transversal end (28), thereby forming a tube of film,
   (c) removing said tube of film from said holding means, thereby obtaining a tampon packaging,
characterized in that
   said heat sealing step (b) is performed at least partly during a combined movement of said holding means (1, 18) and said strip (23).

2. Method according to claim 1, comprising the step of:
   (b1) at least partly heat sealing a longitudinal end of said strip (23),
   said step (b1) being performed after step (a) and before step (c), and before, during or after step (b), thereby obtaining a tube of film with one at least partially closed longitudinal end and one open longitudinal end.

3. Method according to claim 2, wherein prior to step (b1), said longitudinal end of said strip (23) is folded at least partly inwards.

4. Method according to claim 3, wherein said longitudinal end of said strip (23) is folded at least partly inwards by folding said longitudinal end of said strip over a longitudinal end of said holding means (1, 18).

5. Method according to claim 1, wherein said holding means (1, 18) and said strip are at least partly moving rotationally during said heat sealing step (b).

6. Method according to claim 1, wherein said holding means (1, 18) is attached to a conveying means (30) for moving said holding means.

7. Method according to claim 6, wherein said conveying means (30) is moving rotationally.

8. Method according to claim 1, comprising the step of:
   (a1) supplying said strip of film (23) to said holding means (1, 18) via an inlet of said conveying means (30), prior to said heat-sealing step (b) and optionally prior to a heat-sealing step (b1) for at least partly heat sealing a longitudinal end of said strip (23), wherein said supplying step (a1) is performed at least partly simultaneously with said wrapping step (a).

9. Method according to claim 1, characterized in that said strip of film (23) is a thermoplastic material.

10. Method according to claim 1, wherein said strip of film comprises cellulose.

11. Method according to claim 1, characterized in that said strip of film (23) is a heat-shrinkable material.

12. Method for manufacturing a packaged tampon, comprising the steps of:
   providing a tampon;
   manufacturing a tube-like tampon packaging (24) according to claim 1, said tampon packaging (24) comprising at least one open longitudinal end and one at least partially closed longitudinal end;
   combining said tampon packaging (24) with said tampon by:
      inserting said tampon into said tampon packaging (24) via said open longitudinal end, or
      sliding said tampon packaging (24) via said open longitudinal end over said tampon;
   optionally subsequently at least partially closing said open end,
thereby obtaining a packaged tampon.

13. Method according to claim 12, characterized in that the step of combining the tampon packaging (24) with the tampon is performed after or during step (c) of removing the tampon packaging from the holding means (1, 18).

14. Method according to claim 12, wherein said strip of film comprises cellophane.

15. Method according to claim 12, wherein said open end is closed by heat sealing.

16. Tampon packaging manufacturing apparatus comprising a conveying means, which comprises
   at least one holding means (1, 18) for holding a heat-sealable strip of film (23) wrapped around said holding means (1, 18), the holding means (1, 18) attached to said conveying means for movement of the holding means in a conveyance direction, and
   at least one heating element (2),
said holding means (1, 18) and said heating element (2) being movable with respect to each other such that a heat-sealable strip of film (23) wrapped around said holding means (1, 18) can be pressed between said holding means (1, 18) and said heating element (2) and subsequently released, characterized in that said heating element (2) is attached to said conveying means for movement of the heating element (2) in the conveyance direction, and that said heating element (2) is arranged to press and heat-seal a heat-sealable strip of film (23) wrapped around said holding means during movement of said conveying means in said conveyance direction between a first stage (A) and a second stage (B).

17. Tampon packaging manufacturing apparatus according to claim 16, wherein the conveying means comprises a rotatable essentially circular wheel and the conveyance direction is an angular direction around a center axis of said wheel.

18. Tampon packaging manufacturing apparatus according to claim 17, comprising:
   a number of holding means for holding a heat-sealable strip of film wrapped around said holding means, each of the holding means attached to said wheel, said number of holding means between 2 and 10, and
   an equal number of heating elements, each of said heating elements corresponding to one of said holding means, each of said holding means and said heating element corresponding with said holding means being movable with respect to each other such that a heat-sealable strip of film wrapped around said holding means can be pressed between said holding means and said corresponding heating element and subsequently released,
characterized in that each of said heating elements is attached to said wheel, and that each of said heating element is arranged to press and heat-seal a heat-sealable strip of film wrapped around said corresponding holding means during rotation of the wheel between a first stage and a second stage.

19. Tampon packaging manufacturing apparatus according to claim 18, wherein said number of holding means is between 4 and 8.

* * * * *